United States Patent [19]

Dromard et al.

[11] Patent Number: 4,675,384

[45] Date of Patent: Jun. 23, 1987

[54] FRACTIONATION/PURIFICATION OF PLASMA BY ION EXCHANGE CHROMATOGRAPHY

[75] Inventors: Adrien Dromard, Colombes; Michel Exertier, Orsay; Claude Rollin, Corbeil; Jean-Louis Tayot, La Tour de Salvagny; Michel Tardy, Lyons, all of France

[73] Assignees: Rhone-Poulenc Recherches, Courbevoie; Institut Merieux, Lyons, both of France

[21] Appl. No.: 595,823

[22] Filed: Apr. 2, 1984

[30] Foreign Application Priority Data

Apr. 1, 1983 [FR] France .................. 83 05441

[51] Int. Cl.$^4$ .................. A61K 37/02; B01D 15/06
[52] U.S. Cl. .................. 530/364; 530/380; 530/416; 530/417; 424/101; 210/661; 210/666; 210/263; 210/290; 210/927
[58] Field of Search .................. 260/112 R, 112 B, 122; 424/101; 210/661, 663, 263, 290, 927, 666; 530/362, 363, 364, 380, 412, 416, 417

[56] References Cited

U.S. PATENT DOCUMENTS

| | | | |
|---|---|---|---|
| 3,941,718 | 3/1976 | Barabas et al. | 252/430 |
| 4,025,500 | 5/1977 | Garcia et al. | 530/364 |
| 4,086,222 | 4/1978 | Lindquist et al. | 530/364 |
| 4,136,094 | 1/1979 | Condie | 530/364 |
| 4,176,056 | 11/1979 | Grier | 210/661 |
| 4,228,154 | 10/1980 | Fisher et al. | 530/364 |
| 4,229,342 | 10/1980 | Mirabel | 260/122 |
| 4,308,254 | 12/1981 | Tayot et al. | 424/12 |

FOREIGN PATENT DOCUMENTS

| | | | |
|---|---|---|---|
| 2321932 | 8/1975 | France . | |
| 2359634 | 7/1976 | France . | |
| 0115684 | 9/1981 | Japan | 210/661 |
| 1544867 | 4/1979 | United Kingdom . | |

*Primary Examiner*—John Kight
*Assistant Examiner*—Nathan M. Nutter
*Attorney, Agent, or Firm*—Burns, Doane, Swecker & Mathis

[57] ABSTRACT

The plasma proteins contained in a plasma solution thereof are chromatographically fractioned, e.g., to obtain a high purity therapeutic grade albumin product, by successively contacting said plasma solution with at least one anion exchanger and at least one cation exchanger in fixed bed chromatography columns, the contact and exchange medium of chromatography therein also comprising a plurality of at least partially hydrophobic support particulates and a plurality of hydrophilic ion exchanger support particulates.

25 Claims, No Drawings

FRACTIONATION/PURIFICATION OF PLASMA BY ION EXCHANGE CHROMATOGRAPHY

BACKGROUND OF THE INVENTION

1. Field of the Invention

The present invention relates to the chromatographic fractionation of plasma proteins, and, more especially, to the fractionation of plasma by means of ion exchangers to obtain high purity albumin.

2. Description of the Prior Art

The technique most widely used on an industrial level to separate the principal components of plasma, albumin and immunoglobulins, is the Cohn method, the principle of which being based upon the selective precipitation of proteins with the aid of aqueous alcoholic solutions. The processes for precipitation are not perfectly selective and are particularly denaturating; they entail lengthy processing that is labor and cost intensive and the provision of sterile and apyrogenic products is an especially delicate operation.

With the introduction of the ion exchange materials, novel methods have been proposed to continuously separate the proteins from their mixtures in fixed bed columns. These processes are more economical and make it possible to obtain proteins of higher purity, in better yields. However, their application on a large scale in the biological industry is still fraught with a number of difficulties.

Processes for the isolation of the albumin in blood plasma by contact with polysaccharide ion exchangers are described in French Patent No. 2,327,256, and in U.S. Pat. Nos. 4,228,154 and 4,136,094. These processes involve complex preliminary treatments to eliminate the major portion of the impurities, in particular the lipoproteins, and in certain cases the γ-globulins and/or require a subsequent purification of the albumin using molecular sieves to obtain a degree of purity in excess of 98%. These supplemental treatments are difficult to apply industrially and are expensive. Moreover, productivity is low and ill suited for the treatment of large volumes of plasma, the need for which is accentuated by the constantly increasing worldwide demand for such proteins.

The inorganic or mineral supports, in contrast to the polysaccharides, have excellent physical/mechanical properties permitting high degree of filtration, but the adsorption sites of which, as a function of pH and available ionic strength, may result in significant decreases in protein yield.

Processes for the separation of proteins by chromatography on mineral ion exchange supports are described in detail in, for example, French Pat. Nos. 2,321,932, 2,359,634 and 2,464,967. The combination of the ion exchangers described may result, in the case of plasma fractionation, in inadequate yields for the degrees of purity required for therapeutic applications and does not yield high purity albumins regardless of the plasma to be fractionated.

SUMMARY OF THE INVENTION

Accordingly, a major object of the present invention is the provision of an improved process for the treatment of large volumes of plasma and the subsequent isolation, without any supplemental treatment other than the initial clarification of the plasma, of high purity proteins in excellent yields.

Another specific object of the invention is the provision of an improved process for industrial scale extraction of therapeutic grade albumin from plasma, irrespective of the source or origin of the plasma.

Briefly, the present invention features the fractionation of plasma with anionic and cationic ion exchangers and is characterized in that the plasma solution is contacted with at least one partially hydrophobic support, whether or not itself an ion exchanger, and at least one hydrophilic ion exchanger support.

DETAILED DESCRIPTION OF THE INVENTION

The term "partially hydrophobic support" as utilized herein connotes a support comprising hydrophilic and hydrophobic functional groups capable of forming complexes with solutes including lipophilic moieties. Such a support advantageously includes a polymer that is hydrophobic or bears accessible alkyl chains having at least 3 carbon atoms, which may be either linear or branched, saturated or unsaturated, or comprising saturated or unsaturated cyclic ring members. Contrariwise, a hydrophilic support is a support devoid of hydrophobic functions, the available sites at the surface of which being exclusively hydrophilic. These latter supports shall be discussed in more detail below.

In a preferred embodiment of the invention, the subject process is characterized in that a partially desalinized plasma solution is successively contacted with at least one anion exchanger and a cation exchanger. Said ion exchangers have an exchange capacity of less than 2 meq/g, consisting of a porous inorganic support with a grain size distribution of 4 μm to 5 mm, a pore diameter of 500 to 2,500 Å, a specific surface of 5 to 150 $m^2/g$ coated with an amount of less than 15 $mg/m^2$ of a film of a cross linked polymer containing or bearing pendant amine or quaternary ammonium groups as one of the exchangers a cross-linked polyvinyllactam bearing carboxylic acid functions as the other exchanger.

In this particular embodiment of the invention, the mineral supports defining the bases for the ion exchangers comprise the aluminas and the silicas. The exchanger supports may be the same or different and have identical or different characteristics, provided that they remain within the limits described above.

The mineral support preferably has a pore diameter of 600 to 1,500 Å, a specific surface of 20 to 50 $m^2/g$ and a grain size distribution of 50 μm to 1 mm.

The anion exchange resin consists of a cross-linked polymer integrally containing or bearing as pendant functional groups: primary, secondary or tertiary amines, quaternary ammonium salts of the general formulae, $-NH_2$, $-NHR$, $-N(R)_2$, $-N^{(+)}(R)_3X^{(-)}$, wherein each R, which may be identical or different, represents an alkyl or hydroxyalkyl group having from 1 to 4 carbon atoms and X is an inorganic or organic anion, such as, for example, a chloride, sulfate, nitrate, phosphate, citrate, and the like.

The tertiary amine groups and the quaternary ammonium salts comprise an integral part of the cross-linked polymer chain or are pendant therefrom, said polymer chain coating the entire surface of the exchangers, the exchange capacity thereof being less than or equal to 2 meq/g and preferably ranges from 0.15 to 1.2 meq/g and even more preferably from 0.15 to 0.7 meq/g.

The cross-linked polymers coated onto the surfaces of the supports are per se known to the art and are prepared from monomers, such as epoxy compounds, which cross-link with polyamine catalysts; from formaldehyde which cross-links by polycondensation with polyamines; from vinyl monomers, such as vinylpyridine, styrene and derivatives thereof, which cross-link with polyfunctional monomers, such as the diacrylates or dimethylacrylates of the mono- or polyalkylene glycols, divinylbenzene, the vinyltrialkoxysilanes, the vinyltrihalogenosilanes, bis-methyleneacrylamide, in the presence of an initiator or ultraviolet radiation.

In the event that the cross-linked polymer does not include the aforesaid functional groups within or along its chain, it is necessary to modify it. This is especially true for cross-linked polymers based on the styrenes and derivatives thereof, the alkyl acrylates and methacrylates, and for acrylonitrile. This modification of the polymer chain may be effected by any one of a number of known processes.

The supported anion exchange resins and processes for the preparation thereof are described, for example, in published French Applications Nos. 2,321,952 and 2,464,067.

As for the cation exchanger, the porous mineral support is coated by a cross-linked polyvinyllactam film bearing —COOH functional groups.

The vinyllactam copolymers coated onto the support are per se known to the art. These are prepared by copolymerization of monomers of the formula:

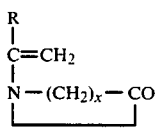
(I)

wherein R is hydrogen or lower alkyl and x is an integer ranging from 2 to 5, with an unsaturated carboxylic acid comonomer of the formula:

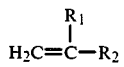
(II)

wherein $R_1$ is hydrogen or $CH_3$ and $R_2$ is a —COOH group, which may be bonded to the unsaturated carbon atom by means of a linear or branched chain divalent alkylene radical having from 1 to 30 carbon atoms, phenylene, cycloalkylene, $-(CH_2)_nO-(CH_2)_m$, $-(CH_2)_nCO-(CH_2)_m$, $-(CH_2)_nCOO-(CH_2)_m$, $-(CH_2)_nSO_2-(CH_2)_m$, $-(CH_2)_nNR_4-(CH_2)_m$, $-(CH_2)_nCO-NR_4-(CH_2)_m$, wherein $R_4$ is hydrogen or an alkyl radical having from 1 to 3 carbon atoms, and n and m are integers ranging from 0 to 12.

Exemplary of the monomers of the formula (I), representative are N-vinylpyrrolidone, N-vinylcaprolactam, N-vinyl-β-propiolactam, 1′α-methylvinylpropiolactam, etc. Preferably, N-vinylpyrrolidone is used.

Exemplary of the carboxylic acid comonomers of the formula (II), representative are acrylic acid, methacrylic acid, 4-pentenoic acid, vinylbenzenecarboxylic acid, 6-acrylamidohexanoic acid, and the like.

These monomers may be cross-linked with the aid of polyfunctional cross-linking agents known to the art, such as, for example, the diacrylates of polyols, such as the diacrylates or dimethacrylates of diethylene glycol or dibutane-1,4-diol, and the vinyl or allyl derivatives of triazine, such as triallylisocyanurate. Also suitable as cross-linking agents are silane type monomers of the formula $CH_2=CH-SiX_3$(III), wherein each X, which may be identical or different, represents a hydrolyzable lower alkoxy, acetoxy or phenoxy radical, or a halogen. Examples of such silane derivatives are vinyltrimethoxysilane, vinyltriethoxysilane, vinyltriacetoxysilane, vinyltrichlorosilane, and vinyl-tris(β-methoxyethoxy)silane.

Preferably, the coating of the mineral support by the copolymer is effected by in situ polymerization of the monomers in the presence of the support. The vinyllactam, the cross-linking agent and the vinylcarboxylic acid, optionally an initiator, are placed in solution in a solvent, then the solution is impregnated onto the support, and the solvent is next evaporated and the monomers cross-linked by any known process, such as by heat or ultraviolet radiation. Suitable for use as the solvent, any compound or composition which is a solvent for the monomers may be used; it should have the lowest possible boiling point to facilitate its subsequent evaporation. Exemplary solvents are, for example, methylene chloride, the chlorofluoromethanes (Flugenes), ethyl ether, acetone, ethyl acetate, and the like.

Generally, the amount of the monomer to be used is selected such as to coat the surface area of the pores of the support with a polymer film weighing from 1 to 15 mg/m², preferably from 1 to 6 mg/m². The ratio of the monomers determines the amount of functional groups distributed over the polymer film. Preferably, vinylcarboxylic acid is used in an amount such that the quantity of functional groups distributed over the surface of the support ranges from 0.05 to 2 meq/g of the support. The amount of the cross-linking agent may vary from 1 to 60% by weight, with respect to the total weight of the monomers.

Thus, it has now surprisingly been found that the separation of plasma proteins providing very high purity albumin may be chromatographically generally achieved on other supports, provided that, successively, at least one ion exchanger support, whether or not at least partially hydrophobic, and at least one hydrophilic ion exchanger support, are used.

In this general aspect of the invention the support may be mineral or organic, natural or synthetic. For reasons of large scale productivity, however, supports based upon the inorganic oxides are preferred.

The hydrophilic supports may consist of polymer matrices or inorganic oxides coated with a hydrophilic polymeric film having ion exchange groups. Examples of natural hydrophilic supports are polymer matrices based on polysaccharides, such as cross-linked dextran, agarose, cross-linked agarose, cellulose, cross-linked cellulose, and the like.

Known synthetic hydrophilic supports may be obtained by polymerization of monomers such as acrylamide and hydrophilic derivatives thereof.

Another group of hydrophilic supports is constituted by porous inorganic oxides, the surface areas of which are coated with a natural or synthetic hydrophilic polymer. The porous inorganic oxide may be silica, alumina, magnesia, titanium dioxide or the natural or synthetic derivatives thereof, such as glasses, silicates, zeolites, kaolin, etc. The inorganic or mineral support has a grain size distribution of 4 μm to 5 mm, preferably 50 μm to 1 mm, a pore diameter ranging from 250 to 3000 Å, preferably from 600 to 1,500 Å, and a specific surface ranging from 5 to 150 m²/g, preferably from 20 to 50 m²/g.

The polymer coating the surface areas of the support may be a natural polysaccharide polymer such as those described above; it may be a known hydrophilic polymer insoluble in water and obtained by the polynerization of vinyl monomers in the presence of a cross-linking agent. Representative examples of these hydrophilic polymers include the polymers of hydroxyalkyl or hydroxy(lower alkoxy)alkyl acrylates and methacrylates, such as the homopolymers and copolymers of 2-hydroxyethyl, hydroxypropyl, and hydroxyethoxyethyl acrylate or methacrylate; the partially hydrolyzed polymers of a vinyl ester of a carboxylic acid, for example the partially hydrolyzed homo- and copolymers of vinyl acetate; the acrylamide polymers; polymers of vinyl heterocyclic compounds, such as the homo- and copolymers of N-vinyllactams, and the like. Mineral oxides coated with polysaccharide polymers are described in French Patent No. 2,319,399.

The partially hydrophobic supports may also consist of natural or synthetic polymers or of mineral oxides such as those defined above, coated with a film of a partially hydrophobic polymer. Polysaccharide polymers may be rendered partially hydrophobic by immobilization with such groups as linear or branched chain alkyl or alkenyl hydrocarbon radicals having at least 3 carbon atoms; aryl or alkylaryl radicals such as phenyl, tolyl and xylyl; cycloalkyl or cycloalkenyl radicals, such as cyclohexyl. The synthetic polymers may be obtained by suspension polymerization of vinylaromatic monomers, such as styrene and derivatives thereof, whether used alone or in a mixture with themselves and/or at least one comonomer copolymerizable therewith, such as, for example, alkyl ($C_1$–$C_5$) acrylates and methacrylates, acrylonitrile, butadiene, and cross-linked by means of polyfunctional monomers, such as mono- or polyalkyleneglycol diacrylates or dimethacrylates, divinylbenzene, vinyltrialkoxysilanes, vinyltrihalogenosilanes, bis-methylene acrylamide, in the presence of an initiator or ultraviolet radiation.

The hydrophobic support preferably used according to the invention consists of a mineral oxide (such as those defined above for the hydrophilic support) coated with an at least partially hydrophobic polymeric film. The coating polymer may be a polysaccharide polymer, upon which hydrophobic groups have been immobilized or fixed, for example, long chain aliphatic amines (such type of support may be prepared by the process described, for example, in French Patent. No. 2,403,098, or U.S. Pat. No. 4,308,254) or a synthetic polymer obtained from monomers such as the epoxy compounds which cross-link with polyamines as the catalysts; formaldehyde which cross-links by polycondensation with polyamines; vinyl monomers, such as vinylpyridine, styrene and derivatives thereof which cross-link with polyfunctional monomers such as mono- or polyalkyleneglycol diacrylates or dimethacrylates, divinylbenzene, vinyltrialkoxysilanes, vinyltrihalogenosilanes, bis-methylene acrylamide, in the presence of an initiator or ultraviolet radiation.

The ion exchange groups may be fixed onto the hydrophilic or hydrophobic polymer by chemical modification or introduced into the polymer chain by polymerization or copolymerization with the aid of vinyl monomers bearing ionizable functional groups of the acid or basic type, or capable of being later modified by chemical reaction to introduce ion exchange radicals. Exemplary copolymerizable monomers which may be used are compounds of the formula:

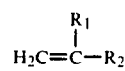

wherein
$R_1$ is hydrogen or $CH_3$ and $R_2$ represents:
(i) an aryl radical such as phenyl or naphthyl;
(ii) a reactive functional group Y such as $-C\equiv N$, $-CONH_2$, $-CH_2OH$, $-COOR_3$ wherein $R_3$ is hydrogen or $C_1$–$C_6$ alkyl or

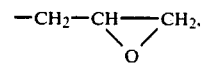

$-OH$, $-NH_2$, -halogen, $-SO_3H$, $-PO(OH)_2$;
(iii) or a functional group Y defined as above, bonded to the unsaturated carbon atom through a bridge comprising a linear or branched chain divalent alkylene $C_1$–$C_{30}$ radical, or a cycloalkylene such radical, $-CH_2)_nO-CH_2)_m$, $-CH_2)_nCO-CH_2)_m$, $-CH_2)_nCOO-CH_2)_m$, $-CH_2)_nSO_2-CH_2)_m$, $-CH_2)_nNR_4-CH_2)_m$, or $-CH_2)_nCO-NR_4-CH_2)_m$, wherein $R_4$ is hydrogen or $C_1$–$C_3$ alkyl and n and m are integers ranging from 0 to 12.

Exemplary monomers copolymerizable therewith, the following are representative: (meth)acrylic acid, 4-pentenoic acid, vinylbenzene sulfonic acid, vinylbenzene carboxylic acid, acrylamide and methacrylamide, acrylonitrile and methacrylonitrile, allyl alcohol, allyl amine, 1,2-dimethyl-4-pentenylamine, 2,3-epoxypropyl acrylate and methacrylate, n-methylolacrylamide, 6-acrylamidohexanoic acid, styrene, and the like.

The selection of the reactive vinyl monomer to provide the functional copolymer is limited only by the intended use of the functional group. It is possible, for example, to select a monomer bearing a cationic or an anionic functional group and to use the support directly as an ion exchange resin.

If the monomer itself does not contain the ion exchange group, it is possible to later modify it by chemical reaction according to any known process to the extent that the reaction is compatible with the stability of the copolymer.

It is also possible to later modify the reactive group Y present in the copolymer by any conventional method to obtain a new functional group Y'. This modification may consist, for example, of converting a primary amine to a tertiary amine or a quaternary ammonium salt to prepare an anion exchange support, or to convert a cation exchanger into an anionic exchanger by reaction of a diamine with the $-COOH$ group, and then converting the reaction product into a quaternary ammonium salt by alkylation.

The coating of the mineral support with the natural or synthetic polymer is provided by any convenient method, such as pulverization or impregnation. When the coating polymer is a synthetic polymer, the coating is preferably applied by the impregnation of the support with a solution of the aforesaid monomer or monomers and, optionally, a polymerization initiator, in any suitable solvent, which solvent is subsequently evaporated and the monomers cross-linked by known processes. Suitable for use as the solvent, any material capable of dissolving the monomers and the initiator may be used. The boiling point of the solvent should be as low as possible to facilitate its subsequent evaporation. Exemplary such solvents are methylene chloride, ethyl ether, benzene, acetone, ethyl acetate, the chlorofluoromethanes (Flugenes), and the like.

In general, the amount of monomer or monomers or the polymer to be used is selected such as to provide on the surface area of the support a polymeric film weighing from 1 to 15 mg/m$^2$ and preferably from 1 to 6 mg/m$^2$.

The amount of functional groups distributed over the surface of the support advantageously ranges from 0.01 to 2 meq/g of the support. When the supports are themselves used as the ion exchangers, this amount preferably ranges from 0.05 to 2 meq/g of the support.

The anion exchange functional groups may comprise aminoaromatic or aminoaliphatic groups, such as, preferably, the diethylaminoethyl group or quaternary aminoalkyl groups of the formula $-N^+-R)_3X^{(-)}$, wherein each R, which may be identical or different, represents an alkyl or hydroxyalkyl group and X represents an organic or inorganic anion, such as, for example, a chloride, sulfate, nitrate, phosphate, citrate, borate, acetate, formate, or the like.

The cation exchange functional groups may comprise a sulfonate, sulfate, phosphono, carboxyl or phenolic hydroxyl groups, preferably carboxymethyl or sulfoalkyl groups.

Among the commercially available hydrophilic ion exchanger supports, the following are representative: compounds marketed under the trademarks Sephadex and Sepharose, products of Pharmacia Fine Chemicals AB, in particular DEAE Sephadex (diethylaminoethyldextran), QAE Sephadex (quaternized diethylaminoethyldextran), DEAE Sepharose (diethylaminoethylagarose), CM Sephadex (carboxymethyldextran), SP Sephadex (sulfopropyldextran), CM Sepharose (carboxymethylagarose), together with the compounds marketed as DEAE Trisacryl M and CM Trisacryl M, products of Societe Chimique Pointet-Girard.

Among the partially hydrophobic supports, the following are exemplary: the products marketed as Phenyl-Sepharose CL-4B, Octyl-Sepharose CL-4B (Pharmacia Fine Chemicals AB), which are based on cross-linked agarose; Spherosil Q MA (Rhone-Poulenc Recherches), which is a silica coated with a polymer based on vinyl toluene and including quaternary ammonium groups.

The starting material plasmas used according to the invention may be of animal origin, bovine plasma in particular, or human. Such plasmas are readily obtained by decantation or centrifugation of blood, or by ultrafiltration on plasmaphoresis cells. Completely fresh or frozen plasma may be used, or a supernatant of a cryoprecipitate or, particularly, fractions emanating from another separation process.

The plasma to be treated by ion exchange is initially purified to at least in part remove the salts therein, and advantageously also its euglobulins, which are unstable protein complexes. These preliminary treatments do not require the use of clarification or precipitation adjuvants, such as polyethylene glycols or adsorption aids, such as powdered pyrogenic silica. It will be appreciated, however, that the process of the invention is also applicable to plasma solutions which have in fact been subjected to such treatments.

Desalination and adjustment of the pH and resistivity may be accomplished in particular, by diafiltration or permeation chromatography. In another embodiment of the invention, desalination is effected by permeation chromatography on a porous mineral support, the pores of which are coated with a hydrophilic polymer film, such as, for example, cross-linked polyvinyllactam. The mineral support used for this operation advantageously has a pore diameter of from 40 to 300 Å, a specific surface of 100 to 800 m$^2$/g and a grain size distribution of 4 μm to 5 mm.

The coating may be provided by simple adsorption of the polymer onto the support, but in a preferred embodiment of the invention, the coating is effected by in situ polymerization using a solution of an N-vinyllactam, for example, N-vinylpyrrolidone, in the presence of a polyfunctional cross-linking agent selected from among those above exemplified and in the manner above-described for the preparation of the cation exchange resin. Among such cross-linking agents, it is preferred to use a silane derivative which makes it possible to form a stable bond between the mineral support and the polyvinyllactam. The amount of monomers is selected such as to provide on the surface area of the support a polymeric film weighing from 1 to 15 mg/m$^2$, preferably from 1 to 6 mg/m$^2$, with the amount of the cross-linking agent ranging from 1 to 50% by weight with respect to the total weight of the monomers.

Using weakly ionic forces, the plasma may be freed of the euglobulins which it contains at a pH of about 5, followed by centrifugation and separation of the clarified plasma solution.

According to the invention, the plasma solution is contacted with at least one partially hydrophobic support and at least one hydrophilic support. The partially hydrophobic support does not necessarily contain ion exchange groups, but it is necessary to use at least one anion exchanger support and at least one cation exchanger support.

In a preferred embodiment of the invention, to obtain better yields and an albumin of the highest purity, the partially hydrophobic support is an anion exchanger and the hydrophilic support a cation exchanger.

In the most preferred embodiment of the invention, separation is effected by combining two anion exchangers, one of which may be hydrophilic and the other partially hydrophobic, and a hydrophilic cation exchanger. The order of contacting with the latter two is immaterial.

The fractioning of the ionically adjusted and preferably clarified plasma is successively carried out with the anion exchanger or exchangers and with the cation exchanger by adjusting the pH and resistivity such as to selectively fix to the respective ion exchangers either the albumin or the other proteins or impurities.

For example, the plasma solution may be contacted with the partially hydrophobic anion exchanger support previously equilibrated, to fix principally the albumin and the globulins at a pH equal to or greater than 5. By elution, or by means of a buffer solution having a pH ranging from 4.4 to 4.8 and suitably selected ionic attractions, a solution rich in albumin and containing residual α- and β-globulins may be obtained. For example, a pH of 4.7 and a 0.025 M acetate buffer may be used.

The eluted solution, adjusted to a pH of 5.0 or greater is then contacted with the cation exchanger previously equilibrated with a buffer of identical pH, onto which virtually all of the proteins other than albumin are suitably affixed.

In another embodiment of the invention, the plasma solution is successively contacted with a hydrophilic anion exchanger, a partially hydrophobic support, preferably an anion exchanger, and then with a hydrophilic cation exchanger. The pH and the ionic strength of the solution are adjusted as described above to affix the albumin and certain of the α- and β-globulins onto the first hydrophilic anion exchanger. After elution, the solution containing the albumin is contacted with the partially hydrophobic support, upon which different impurities, including the lipoproteins, are affixed at a pH of 4.5 to 6.0 and preferably from 4.7 to 5.2, using a 0.025 to 0.06 acetate buffer. The eluted solution containing the albumin is ultimately purified on the cation exchanger under the conditions indicated above.

The immunoglobulins passing through the anion exchanger support may be purified by being contacted with another ion exchanger support by varying the pH and the ionic strength of the solution.

In a preferred embodiment, wherein mineral oxide supports are used, the amounts of the anion exchangers may range from 250 to 2000 ml per liter of plasma and the amounts of the cation exchanger may range from 200 and 1000 ml per liter. The contact time of the solution with each of the exchangers is advantageously in excess of about 15 minutes.

The process of the invention makes it possible to utilize the entirety of the protein contained in the initial plasma and to obtain an albumin, in solution, having a purity, as determined by electrophoresis using a concentration of 50 g/liter, greater than or equal to 99% and may even be 100%. Analysis by gel filtration demonstrates the absence of albumin polymers. The purity of the albumin solution may be determined by immunoprecipitation methods. In particular, by means of the double immunodiffusion method in gelose, the absence of $\alpha_1$- and β-lipoproteins may be demonstrated; the traces of $\alpha_1$-antitrypsin and haptoglobin that may possibly be detected are not detrimental to the quality of the albumin. This albumin solution may be concentrated by any known process, for example, by ultrafiltration, and then adjusted, stabilized and sterilized for 10 hours at 60° C., to render it useful as an injectable. The proteins other than albumin, which are retained by the exchangers may be eluted by means of a regenerating solution. The mixed proteins contained in the effluent and regenerating solutions may ultimately be separated from one another by chromatographic methods.

The treatment of the plasma may be effected in a vessel discontinuously, semi-continuously, or continuously in a series of columns, the latter option being especially well adapted for industrial applications. The continuous process in a plurality of columns gives rise to markedly enhanced productivity, improved yields and a higher purity of the final products under more favorable conditions of sterility.

In order to further illustrate the present invention and the advantages thereof, the following specific examples are given, it being understood that same are intended only as illustrative and in nowise limitative.

EXAMPLE 1:

The following were prepared:

(1) A support ["A"] for exclusion chromatography (GPC):

200 g of silica having a grain size distribution of 40 to 100 μm, a specific surface of 400 m$^2$/g, an average pore diameter of 80 Å and a pore volume of 1 ml/g were dried at 150° C. under reduced pressure for 5 hours.

The product dry silica was introduced into a homogeneous solution containing 500 ml flugene 11 (CCl$_3$F), 160 ml N-vinylpyrrolidone, 30 ml vinyltriethoxysilane and 1 g dilauroyl peroxide. The flugene 11 was evaporated at ambient temperature and the impregnated silica was then heated to 80° C. for 17 hours to effect crosslinking of the polymer.

The silica was subsequently suspended in 800 ml distilled water and heated to boiling over the course of 5 hours. After filtration, the silica was washed with distilled water, and then acetone, and lastly dried under vacuum at 40° C. Analysis evidenced a carbon content of 12% by weight with respect to the coated silica.

(2) Anion exchanger/support ["B"]:

An anion exchanger on a support consisting of silica having a grain size distribution of 100 to 300 μm, a specific surface of 25 m$^2$/g, an average pore diameter of 1,250 Å and a pore volume of 1 ml/g, was coated with 3.6 mg/m$^2$ of a polymer obtained by the cross-linking of vinyltoluene bearing the functional groups —N$^{(+)}$—CH$_3$)$_3$Cl$^{(-)}$ and had the following characteristics:

(i) Carbon content 6.1%;
(ii) Nitrogen content 0.42%; and
(iii) Ion exchange capacity 0.30 meq/g.

(3) Cation exchanger/support ["C"]:

100 g silica having a grain size distribution of 100 to 300 μm, a specific surface of 25 m$^2$/g, an average pore diameter of 1,250 Å and a pore volume of 1 ml/g were dried at 150° C. under reduced pressure for 5 hours.

The product dried silica was introduced into a solution of 250 ml flugene 11 in which 50 ml N-vinylpyrrolidone, 2 ml acrylic acid, 15 ml vinyltriethoxysilane and 0.50 dilauroyl peroxide were homogenized. Following evaporation of the solvent at ambient temperature, the impregnated silica was heated to 80° C. for 16 hours to effect cross-linking of the resulting polymer coating.

The silica was then suspended in 400 ml distilled water and heated to boiling over the course of 5 hours. After filtration, the silica was washed in distilled water and acetone, then dried under vacuum at 40° C.

The weakly grafted cation exchange silica obtained in this manner had the following characteristics:

(i) %C: 6.05
(ii) %H: 1.09
(iii) %N: 0.3
(iv) Ionic capacity: 0.20 meq/g
(v) Amount of fixed polymer: 3.2 mg/m$^2$ (4) Pre-treatment of the plasma:

Into a column having a diameter of 2.6 cm, were charged 100 g of the support [A] and same were maintained under a state of compression.

Into this column were successively injected, at a flow rate of 30 ml/hour, 200 ml of a 0.025 M sodium acetate buffer, 60 ml of fresh plasma from a plasmaphoresis cell and once again 100 ml of the 0.025 M acetate buffer. All of the proteins were collected in 65 ml of the solution, the resistivity of which was about that of the buffer used.

The pH of the protein solution was adjusted to 5.1 by the slow addition of a 6% acetic acid solution. The euglobulins precipitated were separated by centrifugation.

The protein solution obtained in the foregoing manner had the following characteristics:

(a) Resistivity: 520 Ωcm$^2$/cm;
(b) Total proteins: 43.8 g/liter having the following composition:
(i) Albumin: 66.8%

(ii) α-Globulins: 9.2%
(iii) β-Globulins: 6.6%
(iv) γ-Globulins: 17.4%

(5) Fractionation of the plasma solution:

Into a Column I having a diameter of 1.6 cm, there were charged 25 g of the anion exchanger [B] which were maintained compressed. The column was equilibrated with a 0.025 M sodium acetate buffer at pH 5.1.

Into a Column II having a diameter of 1 cm, there were charged 10 g of the anion exchanger [B] which were maintained compressed. This column was equilibrated with a 0.025 M sodium acetate buffer at pH 4.7.

Into a Column III having a diameter of 1 cm, there were charged 5 g of the cation exchanger [C] which were maintained compressed. This column was equilibrated with a 0.1 M sodium acetate buffer at pH 5.5.

Into the Column I the following materials were successively injected: 58 ml of the pre-treated plasma solution, at a constant flow rate of 70 ml/hour, 100 ml of the 0.025 M sodium acetate buffer solution at a pH of 5.1, and lastly a 0.025 M acetate buffer solution at a pH of 4.7.

185 ml of a solution designated the eluate were recovered from Column I, the total protein content of which was 8.8 g/l and which had the following composition:
(a) Albumin: 93%
(b) α-Globulins: 1.6%
(c) β-Globulins: 3%
(d) γ-Globulins: 2.4%

The yield of extraction of albumin of this column was 89.2%.

130 ml of the eluate from Column I were injected at a constant flow rate of 40 ml/hour into Column II. 110 ml of the 0.025 M acetate buffer at pH 4.7 were then injected into Column II. The effluent and wash solutions were mixed to yield a solution with a total protein content of 4.2 g/l, having the following composition:
(a) Albumin: 96.5%
(b) α-Globulins: 0.8%
(c) β-Globulins: 2.7%

The yield of albumin extraction from Column II was 91.4%.

The solution recovered from Column II was adjusted to pH 5.5 and the resistivity adjusted to 180 $\Omega cm^2/cm$ by addition of sodium chloride. 94 ml of this solution were injected into Column III at a rate of 40 ml/hour. The column was washed with 26 ml of the 0.1 M acetate buffer at pH 5.5. The effluent and wash solutions were mixed to yield a solution having a total protein content of 3.0 g/l, having the following composition:
(a) Albumin: 99.5%
(b) α-Globulins: 0.5%

The yield of albumin extraction from Column III was 94%.

The yield of albumin extraction from the fractionation apparatus was 76.6%.

Columns I and II could be regenerated with a 1 M sodium acetate buffer solution at pH 4.0, while Column III could be regenerated with a 0.5 N HCl solution.

The filtrate (or effluent solution) of Column I contained 75% of γ-globulins and 25% of β-globulins, containing but trace amounts of the α-globulins. This filtrate was injected into a Column IV, which was identical to the Column I, after adjustment to pH 5.8 and an ionic concentration of 0.050 M. A solution was obtained having a purity in γ-globulins of essentially 100%. The total yield of the γ-globulin extraction was 80%.

EXAMPLE 2

100 ml of plasma stored at −40° C. originating from a plasmaphoresis module was slowly defrosted to +4° C. and centrifuged to eliminate the precipitate containing the factor VIII. The plasma obtained, the "cryoprecipitate supernatant", was dialyzed by diafiltration against a 0.005 M acetate buffer at pH 7.4. After the acidification of the solution to pH 5.1 with 6% acetic acid, followed by centrifugation to eliminate the euglobulins, the product protein solution had the following characteristics:
(a) Resistivity: 1.066 $cm^2/cm$;
(b) Total proteins: 39.4 g/liter having the following composition:
(i) Albumin: 67.3%
(ii) α-Globulins: 9.1%
(iii) β-Globulins: 7.2%
(iv) γ-Globulins: 16.3%

Fractionation of the plasma:

58 ml of the immediately-above protein solution were injected at a rate of 70 ml/hour into the Column I, as described in Example 1, containing the anion exchanger [B] and previously equilibrated with a 0.025 M sodium acetate buffer at pH 5.1.

The column was washed with 100 ml of the same buffer solution and then eluted with a 0.025 M acetate buffer solution at pH 4.5.

The eluate collected in this manner (125 ml) had a total protein content of 10.1 g/l and had the following composition:
(a) Albumin: 95.0%
(b) α-Globulins: 1.8%
(c) β-Globulins: 3.2%
(d) γ-Globulins: 0%

The yield of extraction of albumin in this column was 78%.

50 ml of the eluate were injected at a constant flow rate of 40 ml/hour into a second column identical to Column III of Example 1, containing the cation exchanger [C] and previously equilibrated with a 0.1 M acetate buffer at pH 5.5. The column was washed with 15 ml of the same buffer. The effluent and wash solutions were mixed to yield a solution having a total protein content of 7.27 g/l and the following composition:
(a) Albumin: 99.0%
(b) α-Globulins: 1.0%

The yield of albumin from this column was 97.5% and the total yield of extraction of the albumin by the fractionation process was 76%.

EXAMPLE 3

100 ml of bovine plasma obtained by centrifugation were dialyzed by diafiltration against a 0.005 M acetate buffer at pH 7.4.

The protein solution obtained after elimination of the euglobulins as described in the preceding examples, had a resistivity of 1,164 $\Omega\ cm^2/cm$ and a total protein content of 39.1 g/l, and had the following composition:
(a) Albumin: 66.1%
(b) α-Globulins: 8.0%
(c) β-Globulins: 10.0%
(d) γ-Globulins: 15.9%

58 ml of the protein solution were injected at a rate of 70 ml/hour into the Column I described in Example 1, containing the anion exchanger [B] and equilibrated with a 0.025 M acetate buffer at pH 5.1. The column was treated as in the preceding example. The eluate collected (167 ml) contained 7.5 g/l of proteins and had the following composition:
(a) Albumin: 95.3%
(b) α-Globulins: 1.6%
(c) β-Globulins: 3.1%
(d) γ-Globulins: 0%

67 ml of the eluate were then injected at a rate of 40 ml/hour into a second column identical to Column III described in Example 1, containing the cation exchanger and equilibrated with a 0.1 M acetate buffer at pH 5.5. The column was washed with 23 ml of the same buffer.

The effluent and wash solutions were mixed. A solution was obtained having a total protein content of 5.1 g/l and which had the following composition:
(a) Albumin: 99.1%
(b) α-Globulins: 0.9%

EXAMPLE 4

Preparation of the plasma solution:

250 ml of frozen plasma were defrosted at 37° C., adjusted to pH 5.2 with concentrated HCl and dialyzed against 60 l of a 0.01 M phosphate buffer at pH 5.2.

After centrifugation, 293 ml of a plasma solution having a total protein concentration of 35.5 g/l were obtained, and which had the following composition:
(a) Albumin: 56.5%
(b) α-Globulins: 12.9%
(c) β-Globulins: 9.5%
(d) γ-Globulins: 21.1%

Fractionation:

The following elements of apparatus were installed in series:

(I) A Column I (diameter = 1.6 cm), containing 15 g of the partially hydrophobic anion exchanger support [B] described in Example 1;

(II) A Column II (diameter = 1 cm), containing 5 g of the same anion exchanger [B]; and (III) A Column III (diameter = 1 cm), containing 5 g of a cation exchanger support [D] consisting of a silica having a grain size distribution of 100 to 300 μm, a specific surface of 32 m$^2$/g, an average pore diameter of about 1,150 Å and a pore volume of 1.2 ml/g, coated with 5 mg/m$^2$ of a N-vinylpyrrolidoneacrylic acid polymer. This support was prepared in the manner described in Example 1 for the cation exchanger [C], while modifying the monomer ratio. It had the following characteristics:
(i) Carbon content: 8.46%
(ii) Nitrogen content: 1.29%
(iii) Ion exchange capacity: 0.19 meq/g 35 ml of the plasma solution prepared as above were injected at a rate of 60 ml/hour into the Column I, previously equilibrated with a 0.025 M acetate buffer at pH 5.2. After washing the column with 65 ml of the equilibrating buffer solution, at the same rate (60 ml/hour), a 0.025 M acetate buffer was injected at pH 4.7. The effluent solution constituted 160 ml (protein concentration, 3.72 g/l), and had an albumin titer of 92.5%, an α-globulin titer of 3% and a β+γ-globulin titer of 4.5%. An aliquot fraction (138 ml) of the eluate solution was injected at a rate of 40 ml/hour into the Column II, previously equilibrated with a 0.025 M acetate buffer solution having a pH of 4.7. The column was washed with 22 ml of the same buffer solution. The mixture of the effluent and wash solution had a protein concentration of 3.06 g/l and a titer of 93.6% albumin, 2.5% α-globulins and 3.5% β-globulins.

An aliquot fraction (140 ml) of the foregoing mixture of solutions was adjusted to pH 5.5 by the addition of NaOH and to a resistivity of 270 Ω cm$^2$/cm by the addition of 1 M NaCl, injected at a rate of 20 ml/hour into the Column III which was previously equilibrated with a 0.05 M acetate buffer having a pH of 5.5. The column was washed with 25 ml of the same buffer solution.

Electrophoresis carried out on the concentrated mixture of the effluent and wash solution demonstrated the absence of impurities contaminating the albumin (albumin 100%).

The total yield was 71% with respect to the albumin contained in the initial plasma solution.

Columns I, II and III were regenerated by washing with a 0.1 N HCl solution, distilled water and buffer solution, respectively.

EXAMPLE 5

The following were prepared:

(1) A hydrophilic anion exchanger on a porous inorganic support, designated anion exchanger [E]:

100 g porous silica (Spherosil XOB 015) having a grain size distribution of 100-200μ, a specific surface of 30 m$^2$/g, an average pore diameter of 1,250 Å, and a pore volume of 1 ml/g were added to 200 ml of a 7.5% aqueous solution of DEAE Dextran, adjusted to pH 11.5 by the addition of sodium hydroxide thereto.

The paste was dried in a plate oven at 80° C. for 15 hours. To the powder obtained were added 300 ml of a 0.15% solution of 1,4 butanediol/diglycidylether in ethyl ether. The ether was evaporated under a stream of nitrogen at ambient temperature. Cross-linking was then effected by heating at 80° C. for 15 hours.

Prior to its use, the support was washed with the following solutions: 10 volumes of 0.1 N NaOH, 10 volumes of 0.1 N HCl and 10 volumes of ethyl alcohol, and then was dried and stored.

115 g of powder were obtained, containing 13% DEAE Dextran and capable of fixing 0.2 meq Cl ions per gram.

(2) A partially hydrophobic anion exchanger, on a porous inorganic support, designated anion exchanger ["F"]; the support was prepared as in (1) hereinabove, but ultimately contained only 5.7% DEAE Dextran:

100 g of the support were oxidized with 500 ml of a 0.05 M aqueous solution of sodium metaperiodate NaIO$_4$ containing 10 g/l NaCl, for 2 hours at ambient temperature. After washing with a 10 g/l solution of NaCl and ethyl alcohol, the product was dried under a stream of nitrogen at 40° C.

100 g of the oxidized support were added to 100 ml of a 6% solution of hexadecylamine in ethyl alcohol and permitted to stand at ambient temperature for 48 hours.

The reduction of the imine bond formed in this manner to an amine bond was effected by the addition of sodium borohydride, NaBH, to attain a concentration of 0.2 M, in the presence of 50% water. After repeated washing with alcohol and 0.1 N HCl, the support was dried and stored prior to use.

(3) Pre-treatment of the plasma:

200 ml of human plasma, pre-washed with sodium citrate, were added to 200 ml of a 16% aqueous solution of ethanol, at 0° C. The precipitate formed was eliminated by centrifuging. The supernatant was acidified (with 1 N HCl) to pH 5.25 at 4° C. After 2 hours, the precipitate was eliminated by centrifugation and the supernatant diafiltered in an ultrafiltration cell and equilibrated with a 0.01 M phosphate buffer having a pH of 5.25. The euglobulin precipitate was again eliminated by centrifuging and the supernatant obtained filtered by means of a porous membrane having a porosity of $0.2\mu$. Its resistivity was 1,200 $\Omega$ cm$^2$/cm.

(4) Fractionation of the plasma solution:

(I) A Column I having a diameter of 2.5 cm was charged with 50 g (105 ml) of the anion exchanger [E]. The column was equilibrated with a 0.01 M sodium phosphate buffer having a pH of 5.25.

(II) A Column II having a diameter of 2.5 cm was charged with 30 g (63 ml) of the anion exchanger [F]. The column was equilibrated with a 0.054 M sodium acetate buffer having a pH of 5.

(III) A Column III having a diameter of 2.5 cm was charged with 60 g (126 ml) of the cation exchanger [D] described in Example 4. The column was equilibrated with a 0.054 M sodium acetate buffer having a pH of 5.5.

The clarified solution corresponding to 200 ml of plasma, obtained by the pre-treatment process described above, was injected into Column I at a rate of 400 ml/hour. The column was rinsed with 200 ml of a 0.01 M phosphate buffer having a pH of 5.25, whereafter the fixed albumin was eluted with 500 ml of a 0.025 M acetate buffer having a pH of 4.7. The eluate was recovered; its volume was 400 ml.

The eluate obtained in this manner was adjusted to pH 5 by addition of 1N NaOH and NaCl was then added to provide a resistivity of 270 $\Omega$ cm$^2$/cm. This solution was injected into Column II at a rate of 100 ml/hour. The majority of the albumin was not fixed under these conditions and passed through the column with the filtrate. The column was rinsed with 120 ml of 0.054 M sodium acetate, having a pH of 5.

The mixture containing the albumin was adjusted to pH 5.5 by addition of NaOH and injected into Column III at a rate of 200 ml/hour. The column was rinsed with 200 ml of a 0.054 M sodium acetate buffer having a pH of 5.5. The effluent solutions were mixed and concentrated by ultrafiltration on an Amicon PM 10 membrane to provide a concentration of 50 to 200 g/l. The purity of the albumin solution, 50 g/l, was estimated by electrophoresis and immunoelectrophoresis on cellulose acetate under pharmacopoeia conditions. It was 100%. Analysis by double immunodiffusion in gelose with respect to specific antiserums of the different plasma proteins made it possible to verify the absence of protein impurities and in particular of $\alpha$-and $\beta$-lipoproteins. When the final concentration of the purified albumin was 130 g/l, trace amounts of $\alpha_1$-antitrypsin and haptoglobin which were not visible under electrophoresis could be detected by double immunodiffusion with respect to the corresponding antiserums.

The presence of trace amounts of such impurities is normal and of no consequence with regard to the stability of the final product albumin solution, or to tolerance upon intravenous administration to animals or humans.

The results reflecting the yield and purity of the albumin are reported in the following Table.

All three columns are advantageously washed with a 0.1 M, pH 4, acetate solution, or with 20 g/l NaCl, whereby the retained albumin may be recovered for recycle into the next cycle of the process or for independent treatment.

The columns are then regenerated by successive washings with 0.1 N HCl and 60% ethanol. They may be periodically wet sterilized (2% Formol).

EXAMPLE 6

In this example, a hydrophilic anion exchanger support, a hydrophobic anion exchanger support and a hydrophilic cation exchanger support were used.

The following elements of apparatus were installed in series:

(I) A Column I (diameter =1.6 cm) containing 14 g of the anion exchanger support [E] described in Example 5. The column was equilibrated with a 0.01 M phosphate buffer having a pH of 5.2;

(II) A Column II identical to the Column II of Example 4, containing the anion exchanger [B]; and (III) A Column III identical to the Column III of Example 4, containing the cation exchanger [D].

The separation process was carried out as in Example 4, beginning with 61 ml of the same plasma solution and using the same buffer solutions to elute Column I and wash Columns II and III.

The rates of flow from the Columns I, II and III were 60 ml/hour, 20 ml/hour and 20 ml/hour, respectively.

Analysis of the final solution by electrophoresis, concentrated to 50 g/l, demonstrated the absence of impurities contaminating the albumin. Double immunodiffusion testing of the solution, concentrated to 130 g/l, demonstrated the absence of any protein impurity.

The percentage of albumin and column yields are also reported in the Table which follows.

EXAMPLE 7

The separation procedure was carried out as in Example 6, but the order of Columns II and III was reversed.

The eluate issuing from Column I was adjusted to pH 5.5 with NaOH and to a resistivity of 270 $\Omega$ cm$^2$/cm with 1 M NaCl, and injected into Column II.

The solution (effluent +wash) issuing from the Column II was adjusted to pH 4.7 with 1 N HCl, and injected into Column III.

The respective rates of flow were 60 ml/hour, 20 ml/hour and 20 ml/hour.

Analysis by electrophoresis and immunodiffusion of the final solution, concentrated to 130 g/l, demonstrated the absence of impurities contaminating the albumin.

The results, percentage albumin and yields, are also reported in the Table to follow.

EXAMPLE 8

The separation procedure was carried out as in Example 6, but Column II was replaced by a different Column II which contained a partially hydrophobic support which was not an ion exchanger. This support consisted of silica having a grain size distribution of 100 to 300 $\mu$m, a specific surface of 25 m$^2$/g, an average pore diameter of 1,250 Å and a pore volume of 1 ml/g, coated with 3.3 mg/m$^2$ of a cross-linked vinyltoluene/vinyltriethoxysilane polymer having a carbon content of 7.3.

Column II was equilibrated with 50 ml of 95% ethanol and then with a 0.025 M, pH 4.7, acetate buffer solution.

The rates of flow from the Columns I, II and III were 60 ml/hour, 20 ml/hour and 20 ml/hour, respectively.

The effluent solution from Column III had a titer of 99.3% albumin and 0.7% $\alpha$-globulins.

The results of this Example are also reported in the Table to follow.

EXAMPLE 9

The separation procedure was carried out under the same conditions as in Example 5, but the Column III was replaced by a column of CM Sepharose CL-6B (Pharmacia Fine Chemicals, Uppsala, Sweden) of the same size and operated under the same conditions.

The results of this Example are also reported in the Table to follow.

EXAMPLE 10

The separation procedure was carried out under the same conditions as in Example 6, but the Column III was replaced by a column of CM Trisacryl-M (Reagent IBF, Pointet-Girard Co., Villeneuve la Garenne, France) of the same size and operated under the same conditions.

The results of this Example are also reported in the Table to follow.

EXAMPLE 11

The separation procedure was carried out under the conditions of Example 9, but the Column I was replaced by a column of DEAE Sepharose CL 6B (Pharmacia Fine Chemicals, Uppsala, Sweden) of the same size and operated under the same conditions.

The results of this Example are also reported in the Table to follow.

EXAMPLE 12

The separation procedure was carried out as in Example 10, but the Column I was replaced by a column of DEAE Trisacryl M (Reagent IBF, Pointet-Girard Co., Villeneuve la Garenne, France) of the same size and operated under the same conditions.

The results of this Example are also reported in the Table to follow.

EXAMPLE 13

(I) A Column I having a diameter of 2.5 cm was charged with 100 g (210 ml) of the anion exchanger E described in Example 5. The column was equilibrated with a 0.025 M, pH 5.25, sodium acetate buffer.

(II) A Column II having a diameter of 2.5 cm was charged with 63 ml Sepharose CL 4B, with hexadecylamine grafted thereon, and was equilibrated with a 0.054 M, pH 5, sodium acetate buffer. The grafting of the hexadecylamine was carried out using cyanogen bromide, as follows:

100 ml Sepharose CL 4B were washed with deionized water in 3 successive decantings and 200 ml water were added thereto. The pH was maintained at 11 by continuous addition of NaOH, and 9 g BrCN were then added. The reaction time was approximately 15 minutes. When the pH of the reaction medium reached equilibrium, the support was rinsed with 0.1 M bicarbonate and then with 95% ethyl alcohol.

20 g hexadecylamine were dissolved in 200 ml alcohol and added to the support at 40° C. The reaction time was 15 hours.

Lastly, the support was successively washed several times with solutions of 0.1 N HCl and 95% alcohol, then equilibrated as indicated above.

(III) A Column III having a diameter of 2.5 cm was charged with 60 g (126 ml) of the cation exchanger [D] described in Example 4. The column was equilibrated with a 0.054 M, pH 5.5, sodium acetate buffer.

Pre-treatment of human plasma:

200 ml of cryoprecipitate supernatant were added to 200 ml of a 16% aqueous solution of ethanol, at 0° C. The precipitate which formed was eliminated by centrifugation. The supernatant was acidified (with 1N HCl) at pH 5.25, at +4° C. After 2 hours, the precipitate which formed was eliminated by centrifugation and the supernatant diafiltered in an ultrafiltration cell and equilibrated with a 0.025 M, pH 5.25, acetate buffer. The euglobulin precipitate was again eliminated by centrifugation and the resulting supernatant was filtered with a membrane having a porosity of $0.2\mu$. Its resistivity was 630 $\Omega$ cm$^2$/cm. The solution was injected into Column I at a rate of 400 ml/hour. The column was rinsed with 200 ml of a 0.025 M, pH 4.7, acetate buffer. The eluate was recovered; its volume was 350 ml.

The eluate obtained in this manner was adjusted to pH 5 by the addition of NaOH and then NaCl was added to provide a resistivity of 270 $\Omega$ cm$^2$/cm. The solution was injected into Column II at a rate of 100 ml/hour.

A more than negligible amount of albumin was fixed to the exchanger resin in the column, reducing the yield to 20 to 30% with respect to the supports used in Column II in the preceding examples. The solution which passed through the column contained albumin and some of the $\alpha$- and $\beta$-globulins. The column was rinsed with 120 ml of 0.054 M, pH 5, sodium acetate buffer. The mixture containing the albumin was adjusted to pH 5.5 by the addition of NaOH and injected into Column III at a rate of 200 ml/hour. The column was rinsed with 200 ml of the 0.054 M, pH 5.5, sodium acetate buffer. The effluent solutions were admixed and concentrated by ultrafiltration using an Amicon PM 10 membrane to provide a concentration of 50 g/l.

The purity of the solution, estimated by electrophoresis in cellulose acetate under pharmacopoeia conditions was 99.1% and was thus considered satisfactory under applicable standards. Analysis by double immunodiffusion in gelose with respect to specific antiserums of the different plasma proteins made it possible to detect the presence of the following impurities: transferine, $\alpha_1$-antitrypsin, $\beta_2$-macroglobulin, haptoglobulin.

The three columns are advantageously regenerated and sterilized between each cycle as in the proceding examples.

The total yield of the purification process was only 55%.

The results of this Example are also reported in the Table to follow:

EXAMPLE 14 (Comparative)

The separation process was carried out under the same conditions as in Example 13, but the Column II of hydrophobic Sepharose was replaced by a column of the hydrophilic anion exchanger [E]. The results obtained (also reported in the Table to follow) differed from those of the preceding examples. The final purity of albumin was less than 99%. In particular, the systematic presence of $\alpha_1$-lipoprotein was detected; its presence is detrimental to the stability of the final albumin solution, especially upon heating to 60° C.

This Example demonstrates the need to include a filtration stage for the partially hydrophobic support, in order to obtain a very high purity albumin.

TABLE

| EXAMPLE | % ALBUMIN (ELECTROPHORESIS) | | | YIELD IN ALBUMIN (%) | | | |
|---|---|---|---|---|---|---|---|
| | Eluate COLUMN I | After COLUMN II | After COLUMN III | COLUMN I | COLUMN II | COLUMN III | TOTAL |
| 4  | 92.5 | 93.6 | 100  | 78.5 | 96.5 | 93.6 | 71 |
| 5  | 93.7 | 96.5 | 100  | 79   | 92   | 98   | 71 |
| 6  | 93.7 | 96.2 | 100  | 79   | 91.3 | 98   | 71 |
| 7  | 93.7 | 96.6 | 100  |      |      |      | 78 |
| 8  | 93.7 | 94.9 | 99.3 |      |      |      | 67 |
| 9  | 92.8 | 96.5 | 100  |      |      |      | 75 |
| 10 | 94   | 96.8 | 100  |      |      |      | 72 |
| 11 | 92.5 | 96.2 | 100  |      |      |      | 69 |
| 12 | 93.0 | 96.5 | 100  |      |      |      | 73 |
| 13 | 94.2 | 94.7 | 99.1 |      |      |      | 55 |
| 14 | 94.2 | 94.3 | 97   |      |      |      | 79 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. In a process for the chromatographic fractionation of the plasma proteins contained in a plasma solution thereof by successively contacting said plasma solution with at least one anion exchanger and at least one cation exchanger, the improvement which comprises contacting said plasma solution with a contact and exchange chromatography medium comprising a plurality of at least partially hydrophobic support particulates and a plurality of hydrophilic ion exchanger support particulates.

2. The process as defined by claim 1, said at least partially hydrophobic support particulates themselves comprising ion exchangers.

3. The process as defined by claim 1, said at least partially hydrophobic support particulates being incapable of ion exchange.

4. The process as defined by claim 2, said at least partially hydrophobic support particulates comprising anion exchangers and said hydrophilic support particulates comprising cation exchangers.

5. The process as defined by claim 1, said hydrophilic support particulates comprising cation exchangers.

6. The process as defined by claim 4, said at least partially hydrophobic support particulates comprising anion exchangers and said hydrophilic support particulates comprising both anion and cation exchangers.

7. The process as defined by claim 6, wherein the plasma solution is contacted with the hydrophilic anion exchanger support particulates upstream of contact with the at least partially hydrophobic anion exchanger support particulates.

8. The process as defined by claim 1, said support particulates each comprising a natural polysaccharide polymer, a synthetic polymer, inorganic oxides coated with a polysaccharide polymer, or inorganic oxides coated with a cross-linked synthetic polymer.

9. The process as defined by claim 1, said at least partially hydrophobic support particulates comprising a polysaccharide polymer including hydrophobic moieties, a synthetic polymer adsorbent, inorganic oxides coated with a polysaccharide polymer including hydrophobic moieties, or inorganic oxides coated with a cross-linked hydrophobic polymer.

10. The process as defined by claim 1, said hydrophilic ion exchanger support particulates comprising a polysaccharide polymer, a water-insoluble synthetic hydrophilic polymer, inorganic oxides coated with a polysaccharide polymer, or inorganic oxides coated with a cross-linked hydrophilic polymer.

11. The process as defined by claim 1, said at least partially hydrophobic support particulates and said hydrophilic ion exchanger support particulates comprising porous inorganic oxides having a grain size distribution ranging from 4 μm to 5 mm, pore diameters ranging from 250 to 3,000 Å, and a specific surface ranging from 5 to 150 m$^2$/g.

12. The process as defined by claim 11, said grain size distribution ranging from 50 μm to 1 mm, said pore diameters ranging from 600 to 1,500 Å, and said specific surface ranging from 20 to 50 m$^2$/g.

13. The process as defined by claim 1, said at least one anion exchanger and said at least one cation exchanger having an ion exchange capacity of less than about 2 meq/g and comprising porous inorganic particulates having a grain size distribution ranging from 4 μm to 5 mm, pore diameters ranging from 500 to 2,500 Å, and a specific surface ranging from 5 to 150 m$^2$/g.

14. The process as defined by claim 13, porous inorganic particulates coated with less than about 15 mg/m$^2$ of a cross-linked hydrophobic polymer including amine or quaternary ammonium salt functions comprising at least one of said ion exchangers, and porous inorganic particulates coated with less than about 15 mg/m$^2$ of a cross-linked polyvinyllactam polymer bearing carboxylic acid functions comprising another ion exchanger.

15. The process as defined by claim 1, further comprising contacting said plasma solution with porous inorganic particulates having a grain size distribution ranging from 4 μm to 5 mm, pore diameters ranging from 500 to 2,500 Å, and a specific surface ranging from 5 to 150 m$^2$/g, said particulates being coated with less than 15 mg/m$^2$ of a polysaccharide polymer bearing amine or quaternary ammonium salt functions.

16. The process as defined by claim 14, at least one cation exchanger comprising the polyvinyllactam polymer coated particulates, said polymer being prepared by copolymerization of a vinyllactam and an unsaturated carboxylic acid comonomer in the presence of a polyfunctional cross-linking agent.

17. The process as defined by claim 16, said vinyllactam comprising N-vinylpyrrolidone.

18. The process as defined by claim 16, said unsaturated carboxylic acid comonomer comprising acrylic acid.

19. The process as defined by claim 16, said cross-linking agent comprising a silane derivative of the formula $CH_2=CH-SiX_3$, wherein each x, which may be identical or different, is hydrolyzable lower alkoxy, acetoxy or phenoxy radical, or a halogen.

20. The process as defined by claim 14, at least one anion exchanger comprising particulates coated with a hydrophobic cross-linked polymer prepared from vinylaromatic monomers.

21. The process as defined by claim 1, comprising employing from 250 to 2,000 ml of anion exchangers and 200 to 1,000 ml of cation exchangers per liter of plasma solution contacted.

22. The process as defined by claim 1, said chromatographic fractionation being carried out continuously and successively in a series of chromatography columns packed with said anion and cation exchangers and said at least partially hydrophobic and said hydrophilic support particulates.

23. The process as defined by claim 1, wherein albumin is selectively fractioned from the other plasma proteins.

24. The process as defined by claim 1, said beginning plasma solution being at least partially desalinized.

25. An at least 99% pure albumin, as determined by electrophoresis, prepared by the process as defined by claim 1.

* * * * *